United States Patent
Luk et al.

(10) Patent No.: US 11,220,538 B2
(45) Date of Patent: Jan. 11, 2022

(54) MONOCLONAL ANTIBODIES AGAINST ALPHA-SYNUCLEIN FIBRILS

(71) Applicant: The Trustees of the University of Pennsylvania, Philadelphia, PA (US)

(72) Inventors: Kelvin C. Luk, Philadelphia, PA (US); Virginia M. Y. Lee, Philadelphia, PA (US); John Q. Trojanowski, Philadelphia, PA (US); Kurt R. Brunden, Media, PA (US); Dustin Covell, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/609,885

(22) PCT Filed: May 1, 2018

(86) PCT No.: PCT/US2018/030436
§ 371 (c)(1),
(2) Date: Oct. 31, 2019

(87) PCT Pub. No.: WO2018/204352
PCT Pub. Date: Nov. 8, 2018

(65) Prior Publication Data
US 2020/0062835 A1    Feb. 27, 2020

Related U.S. Application Data

(60) Provisional application No. 62/492,663, filed on May 1, 2017.

(51) Int. Cl.
| | |
|---|---|
| C07K 16/18 | (2006.01) |
| A61P 25/28 | (2006.01) |
| G01N 33/577 | (2006.01) |
| G01N 33/68 | (2006.01) |
| A61K 39/00 | (2006.01) |
| A61K 9/00 | (2006.01) |

(52) U.S. Cl.
CPC ............ *C07K 16/18* (2013.01); *A61K 9/0029* (2013.01); *A61P 25/28* (2018.01); *G01N 33/577* (2013.01); *G01N 33/6896* (2013.01); *A61K 2039/505* (2013.01); *C07K 2317/24* (2013.01); *C07K 2317/34* (2013.01); *C07K 2317/565* (2013.01); *C07K 2317/92* (2013.01)

(58) Field of Classification Search
CPC .............. C07K 16/18; C07K 2317/24; C07K 2317/34; C07K 2317/565; C07K 2317/92; A61P 25/28; A61K 9/0029; A61K 2039/505; G01N 33/577; G01N 33/6896
See application file for complete search history.

(56) References Cited

U.S. PATENT DOCUMENTS

| | | |
|---|---|---|
| 2008/0300204 A1 | 12/2008 | Federoff et al. |
| 2010/0278814 A1 | 11/2010 | Games et al. |
| 2014/0241984 A1 | 8/2014 | El-Agnaf et al. |
| 2014/0241987 A1 | 8/2014 | El-Agnaf et al. |
| 2014/0275495 A1 | 9/2014 | Saldanha et al. |
| 2015/0139900 A1 | 5/2015 | Nordström et al. |
| 2015/0140003 A1 | 5/2015 | Kaluza et al. |
| 2015/0259404 A1 | 9/2015 | Barbour et al. |
| 2017/0015739 A1 | 1/2017 | Kallunki et al. |
| 2017/0114123 A1 | 4/2017 | Kaluza et al. |

FOREIGN PATENT DOCUMENTS

| | | |
|---|---|---|
| EP | 3067066 A1 | 9/2016 |
| WO | 2005047860 A2 | 5/2005 |
| WO | 2007062088 A1 | 5/2007 |
| WO | 2013059885 A2 | 5/2013 |
| WO | 2017009312 A1 | 1/2017 |

OTHER PUBLICATIONS

Rudikoff et al., Proc Natl Acad Sci USA, vol. 79 p. 1979 (Year: 1982).*
Casset et al., BBRC 307, 198-205 (Year: 2003).*
Robert et al., Nature Methods vol. 4, pp. 345-351, 2007 (Year: 2007).*
Fodero-Tavoletti, et al. (2009) In vitro characterisation of BF227 binding to α-synuclein/Lewy bodies. Eur. J. Pharmacol. 617, 54-58. (Year: 2009).*
International Search Report for International Application No. PCT/US2018/030436 dated Jul. 19, 2018.
Covell, et al., "Novel conformation-selective alpha-synuclein antibodies raised against different in vitro fibril forms show distinct patterns of Lewy pathology in Parkinson's disease," Neuropathol Appl. Neurobiol., vol. 43, May 2017, pp. 604-620.
El-Agnaf, et al., "Different effects of immunotherapy wit antibodies targeting α-synuclein oligomers and fibrils in a transgenic model of synucleinopathy," Neurobiol Dis., vol. 104, Aug. 2017, pp. 85-96.

(Continued)

*Primary Examiner* — Kimberly Ballard
*Assistant Examiner* — Stacey N MacFarlane
(74) *Attorney, Agent, or Firm* — Saul Ewing Arnstein & Lehr LLP; Domingos J. Silva

(57) ABSTRACT

The present disclosure provides monoclonal antibodies that bind α-Synuclein. In certain aspects, the antibodies preferentially bind to α-Synuclein fibrils over α-Synuclein monomer. In other aspects, the invention comprises a method of treating α-Synucleopathic disease in a subject, comprising administering any of the antibodies of the invention to the subject. In yet other aspects, the invention comprises methods of detecting α-Synuclein fibrils using any of the antibodies of the invention.

23 Claims, 4 Drawing Sheets
Specification includes a Sequence Listing.

(56) References Cited

OTHER PUBLICATIONS

Guo, et al., "Distinct α-Synuclein Strains Differentially Promote Tau Inclusions in Neurons," Cell, vol. 154, No. 1, Jul. 2013.
Lashuel, et al., "The many faces of α-synuclein: from structure and toxicity to therapeutic target," Nat Rev Neurosci., vol. 14, No. 1, Jan. 2013, pp. 38-48.
Lindstrom, et al., "Immunotherapy targeting α-synuclein protofibrils reduced pathology in (Thy-1)-h[A30P] α-synuclein mice," Neurobiology of Disease, vol. 69, Sep. 2014, 134-143 (Abstract only).
Lindstrom, et al., "Immunotherapy targeting α-synuclein, with relevance for future treatment of Parkinson's disease and other Lewy body disorders," Immunotherapy, vol. 6, No. 2, Feb. 2014, 141-153 (Abstract only).
Luk, et al., "Exogenous α-synuclein fibrils seed the formation of Lewy body-like intracellular inclusions in cultured cells," PNAS, vol. 106, No. 6, Nov. 2009, pp. 20051-20056.
Sahin, et al., "Antibodies against the C-terminus of α-synuclein modulate its fibrillation," Biophysical Chemistry, vol. 220, Nov. 2017, pp. 34-41.
Vaikath, et al., "Generation and characterization of novel conformation-specific monoclonal antibodies for α-synuclein pathology", Neurobiol Dis., vol. 79, Apr. 2015, pp. 81-99.
Supplementary Partial European Search Report for European Patent Application No. 18795033.2 dated Dec. 22, 2020.

\* cited by examiner

SEQUENCE LISTING

<160> NUMBER OF SEQ ID NOS: 31

<210> SEQ ID NO 1
<211> LENGTH: 5
<212> TYPE: PRT
<213> ORGANISM: Mus musculus

<400> SEQUENCE: 1

Ser Ser Val Ser Tyr
1               5

<210> SEQ ID NO 2
<211> LENGTH: 3
<212> TYPE: PRT
<213> ORGANISM: Mus musculus

<400> SEQUENCE: 2

Asp Thr Ser
1

<210> SEQ ID NO 3
<211> LENGTH: 9
<212> TYPE: PRT
<213> ORGANISM: Mus musculus

<400> SEQUENCE: 3

Gln Gln Trp Arg Ser Tyr Pro Pro Thr
1               5

<210> SEQ ID NO 4
<211> LENGTH: 106
<212> TYPE: PRT
<213> ORGANISM: Mus musculus

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Arg Ser Tyr Pro Pro Thr
                85                  90                  95

Phe Gly Ala Gly Thr Lys Leu Glu Leu Lys
            100                 105

<210> SEQ ID NO 5
<211> LENGTH: 318
<212> TYPE: DNA
<213> ORGANISM: Mus musculus

<400> SEQUENCE: 5
caaattgttc tcacccagtc tccagcaatc atgtctgcat ctccagggga gaaggtcacc    60
atgacctgca gtgccagctc aagtgtaagt tacatgtact ggtaccagca gaagccagga   120
tcctccccca gactcctgat ttatgacaca tccaagctgg cttctggcgt ccctgttcgc   180
ttcagtggca gtgggtctgg gacctcttac tctctcacaa tcagccgaat ggaggctgaa   240

```
gatgctgcca cttattactg ccagcagtgg agaagttacc cacccacgtt cggtgctggg    300
accaagctgg agctgaaa                                                 318
```

<210> SEQ ID NO 6
<211> LENGTH: 8
<212> TYPE: PRT
<213> ORGANISM: Mus musculus

<400> SEQUENCE: 6

Gly Phe Ser Leu Thr Ser Tyr Gly
1               5

<210> SEQ ID NO 7
<211> LENGTH: 7
<212> TYPE: PRT
<213> ORGANISM: Mus musculus

<400> SEQUENCE: 7

Ile Trp Ser Gly Gly Ser Thr
1               5

<210> SEQ ID NO 8
<211> LENGTH: 14
<212> TYPE: PRT
<213> ORGANISM: Mus musculus

<400> SEQUENCE: 8

Ala Arg Thr Phe Thr Thr Ser Thr Ser Ala Trp Phe Ala Tyr
1               5                   10

<210> SEQ ID NO 9
<211> LENGTH: 120
<212> TYPE: PRT
<213> ORGANISM: Mus musculus

<400> SEQUENCE: 9

Gln Val Gln Leu Lys Gln Ser Gly Pro Gly Leu Val Gln Pro Ser Gln
1               5                   10                  15

Ser Gln Ser Leu Thr Cys Thr Val Ser Gly Phe Ser Leu Thr Ser Tyr
            20                  25                  30

Gly Val His Trp Val Arg Gln Pro Leu Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Arg Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ala
        115                 120

<210> SEQ ID NO 10
<211> LENGTH: 360
<212> TYPE: DNA
<213> ORGANISM: Mus musculus

<400> SEQUENCE: 10

```
caggtgcagc tgaagcagtc aggacctggc ctagtgcagc cctcacagag ccagtccctg    60
```

```
acctgcacag tctctggttt ctcattaact agttatggcg tacactgggt tcgccagcct    120
ctaggaaagg gtctggagtg gctgggagtg atctggagtg gtggaagcac agactataat    180
gctgctttca tatccagact gagcatcagg aaggacaact ccaagagcca gtcttctttt    240
aaaatgaaca gtctgcaagc tgatgacaca gccatatact actgtgccag aacctttact    300
acgtctacct cggcctggtt tgcttactgg ggccaaggga ctctggtcac tgtctctgca    360
```

<210> SEQ ID NO 11
<211> LENGTH: 12
<212> TYPE: PRT
<213> ORGANISM: Mus musculus
<400> SEQUENCE: 11

```
Gln Ser Val Leu Tyr Ser Ser Asn Gln Lys Asn Tyr
1               5                   10
```

<210> SEQ ID NO 12
<211> LENGTH: 3
<212> TYPE: PRT
<213> ORGANISM: Mus musculus
<400> SEQUENCE: 12

```
Trp Ala Ser
1
```

<210> SEQ ID NO 13
<211> LENGTH: 8
<212> TYPE: PRT
<213> ORGANISM: Mus musculus
<400> SEQUENCE: 13

```
His Gln Tyr Leu Ser Leu Phe Thr
1               5
```

<210> SEQ ID NO 14
<211> LENGTH: 112
<212> TYPE: PRT
<213> ORGANISM: Mus musculus
<400> SEQUENCE: 14

```
Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Met Leu Ile Tyr Trp Ala Ser Phe Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Leu Phe Thr Phe Gly Ser Gly Thr Lys Leu Glu Ile Lys
            100                 105                 110
```

<210> SEQ ID NO 15
<211> LENGTH: 336
<212> TYPE: DNA
<213> ORGANISM: Mus musculus -continued

```
<400> SEQUENCE: 15
aacattatga tgacacagtc gccatcatct ctggctgtgt ctgcaggaga aaaggtcact      60
atgagctgta agtccagtca aagtgtttta tacagttcaa atcagaagaa ctacttggcc     120
tggtaccagc agaaaccagg gcagtctcct aaaatgctga tctactgggc atcctttagg    180
gaatctggtg tccctgatcg cttcacaggc agtggatctg ggacagattt tactcttacc    240
atcagcagtg tacaagctga agacctggca gtttattact gtcatcaata cctctcctta    300
ttcacgttcg gctcggggac aaagttggaa ataaaa                              336
```

```
<210> SEQ ID NO 16
<211> LENGTH: 8
<212> TYPE: PRT
<213> ORGANISM: Mus musculus

<400> SEQUENCE: 16

Gly Tyr Thr Phe Thr Thr Phe Tyr
1               5
```

```
<210> SEQ ID NO 17
<211> LENGTH: 8
<212> TYPE: PRT
<213> ORGANISM: Mus musculus

<400> SEQUENCE: 17

Ile Tyr Pro Val Asn Val Lys Ile
1               5
```

```
<210> SEQ ID NO 18
<211> LENGTH: 9
<212> TYPE: PRT
<213> ORGANISM: Mus musculus

<400> SEQUENCE: 18

Val Arg Gly Gly Arg Gly Leu Asp Tyr
1               5
```

```
<210> SEQ ID NO 19
<211> LENGTH: 116
<212> TYPE: PRT
<213> ORGANISM: Mus musculus

<400> SEQUENCE: 19

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Thr Phe
            20                  25                  30

Tyr Leu His Trp Val Lys Gln Arg Pro Gly Gln Gly Leu Glu Trp Ile
        35                  40                  45

Gly Trp Ile Tyr Pro Val Asn Val Lys Ile Lys Tyr Ser Glu Arg Phe
    50                  55                  60

Lys Gly Lys Ala Thr Leu Thr Ala Asp Lys Ser Ser Thr Ala Tyr
65                  70                  75                  80

Met Gln Leu Gly Ser Leu Thr Ser Glu Asp Ser Ala Val Tyr Phe Cys
                85                  90                  95

Val Arg Gly Gly Arg Gly Leu Asp Tyr Trp Gly Gln Gly Thr Thr Leu
            100                 105                 110

Thr Val Ser Ser
        115
```

<210> SEQ ID NO 20
<211> LENGTH: 348
<212> TYPE: DNA
<213> ORGANISM: Mus musculus

<400> SEQUENCE: 20
caggtccagc tgcagcagtc tggacctgag ctggtgaagc ctggggcttc agtgcggata      60
tcctgcaagg cttctggcta caccttcaca accttctatt tacactgggt gaagcagagg     120
cctggacagg gacttgagtg gattggatgg atttatcctg taaatgttaa aattaagtac     180
agtgagaggt tcaagggcaa ggccacactg actgcagaca atcctccag cacagcctac      240 atgcagctcg gcagcctgac ctctgaggac tctgcggtct atttctgtgt aagagggggg     300
aggggacttg actactgggg ccaaggcacc actctcacag tctcctca                  348

<210> SEQ ID NO 21
<211> LENGTH: 5
<212> TYPE: PRT
<213> ORGANISM: Mus musculus

<400> SEQUENCE: 21

Ser Ser Val Thr Tyr
1               5

<210> SEQ ID NO 22
<211> LENGTH: 3
<212> TYPE: PRT
<213> ORGANISM: Mus musculus

<400> SEQUENCE: 22

Asp Thr Ser
1

<210> SEQ ID NO 23
<211> LENGTH: 9
<212> TYPE: PRT
<213> ORGANISM: Mus musculus

<400> SEQUENCE: 23

Gln Gln Trp Ser Ser Asn Pro Pro Thr
1               5

<210> SEQ ID NO 24
<211> LENGTH: 106
<212> TYPE: PRT
<213> ORGANISM: Mus musculus

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Arg
            100                 105

<210> SEQ ID NO 25
<211> LENGTH: 318
<212> TYPE: DNA
<213> ORGANISM: Mus musculus

<400> SEQUENCE: 25
caaattgttc tcacccagtc tccagcaatc atgtctgcat ctccagggga gaaggtcacc     60
atgacctgca gtgccagctc aagtgtaact tacatgcact ggtaccagca gaagtcaggc    120
acctccccca aagatggatt tatgacaca tccaaactgg cttctggagt ccctgctcgc     180
ttcagtggca gtgggtctgg gacctcttac tctctcacaa tcagcagcat ggaggctgaa    240
gatgctgcca cttattactg ccagcagtgg agtagtaacc cacccacgtt cggagggggg    300
accaagctgg aaataaga                                                   318

<210> SEQ ID NO 26
<211> LENGTH: 8
<212> TYPE: PRT
<213> ORGANISM: Mus musculus

<400> SEQUENCE: 26

Gly Phe Thr Phe Asn Thr Tyr Ala
1               5

<210> SEQ ID NO 27
<211> LENGTH: 10
<212> TYPE: PRT
<213> ORGANISM: Mus musculus

<400> SEQUENCE: 27

Ile Arg Asn Lys Ser Asn Asn Tyr Ala Thr
1               5                   10

<210> SEQ ID NO 28
<211> LENGTH: 10
<212> TYPE: PRT
<213> ORGANISM: Mus musculus

<400> SEQUENCE: 28

Val Arg Gly Gly Leu Ser Pro Phe Asp Tyr
1               5                   10

<210> SEQ ID NO 29
<211> LENGTH: 119
<212> TYPE: PRT
<213> ORGANISM: Mus musculus

<400> SEQUENCE: 29

Glu Val His Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Asn Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Phe Leu Gln Met Asp Asn Leu Lys Thr Glu Asp Thr Ala Ile Tyr
            85                  90                  95

Tyr Cys Val Arg Gly Gly Leu Ser Pro Phe Asp Tyr Trp Gly Gln Gly
            100                 105                 110

Thr Thr Leu Thr Val Ser Ser
        115

<210> SEQ ID NO 30
<211> LENGTH: 357
<212> TYPE: DNA
<213> ORGANISM: Mus musculus

<400> SEQUENCE: 30
gaggtacacc ttgttgagtc tggtggagga ttggtgcagc ctaaagggtc attgaaactc      60
tcatgtgcag cctctggatt caccttcaat acctacgcca tgcactgggt ccgccaggct     120
ccaggaaagg gtttggaatg ggttgctcgc ataagaaata aagtaataa ttatgcaaca      180 tattatgccg attcagtgaa agacaggttc accatctcca gagatgattc acaaagcatg     240
ctctttctgc aaatggacaa cttgaaaact gaggacacag ccatatatta ctgtgtgaga     300
ggggggttat ctccctttga ctactggggc caaggcacca cactcacagt ctcctca       357

<210> SEQ ID NO 31
<211> LENGTH: 140
<212> TYPE: PRT
<213> ORGANISM: Homo sapiens

<400> SEQUENCE: 31

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

MONOCLONAL ANTIBODIES AGAINST ALPHA-SYNUCLEIN FIBRILS

CROSS-REFERENCE TO RELATED APPLICATIONS

The present application is a 35 U.S.C. § 371 national phase application from, and claims priority to, International Application No. PCT/US2018/030436, filed May 1, 2018, and published under PCT Article 21(2) in English, which is entitled to priority under 35 U.S.C. § 119(e) to U.S. Provisional Patent Application No. 62/492,663, filed May 1, 2017, all of which applications are incorporated herein by reference in their entireties.

STATEMENT REGARDING FEDERALLY SPONSORED RESEARCH OR DEVELOPMENT

This invention was made with government support under grant number NS053488 awarded by National Institute of Neurological Disorders and Stroke (NIH) and grant number T32-AG000255 awarded by National Institutes of Aging (NIH). The government has certain rights in the invention.

BACKGROUND OF THE INVENTION

The fibrillization of α-Synuclein (α-Syn) is considered to play a key role in the pathogenesis of several neurodegenerative diseases, including Parkinson's disease (PD), dementia with Lewy bodies (DLB), and multiple system atrophy (MSA). Genetic studies show various point mutations in α-Syn (A53T, A30P, E46K, H50Q or G51D) and multiplication of the α-Syn gene SNCA lead to familial PD. Cell culture and animal model studies indicate that enhanced oligomerization and aggregation of α-Syn is associated with increased cytotoxicity, while α-Syn oligomers have been shown to be significantly elevated in the brain lysates and cerebrospinal fluid of PD and DLB patients. The significance of α-Syn fibrillization in the pathobiology of synucleinopathies has been reinforced by recent data demonstrating that preformed recombinant α-Syn fibrils can seed the aggregation of endogenous α-Syn both in a variety of neurons cultured from wild-type mice, and in vivo in transgenic and wildtype mice, even from the peripheral to the central nervous system.

Given the central role of α-Syn in the pathogenesis of synucleinopathies, the characterization of its pathology in the brain has relied heavily on the use of α-Syn antibodies, the vast majority of which recognize both the monomeric and the aggregated forms of α-Syn. Hence, there is a need for developing conformation-specific antibodies that can unveil underappreciated α-Syn neuropathology or even reveal novel neuropathological features of PD and related disorders. Furthermore, taking into account that passive immunotherapy against α-Syn has emerged as a very promising strategy for modifying PD and related synucleinopathies, the generation of high-affinity and/or conformation-specific antibodies that recognize α-Syn fibrils may prove to be a useful tool for the treatment of these diseases. This disclosure addresses and meets those needs.

SUMMARY

Provided is an isolated monoclonal antibody, or fragment thereof, which recognizes a conformational epitope comprising amino acids 110-120 of α-Synuclein (α-Syn), and wherein affinity of the antibody for α-Syn fibrils is higher than for α-Syn monomers. In some embodiments, the antibody binds at least about 30 times more tightly to α-Syn fibrils than to α-Syn monomers.

Provided is an isolated monoclonal antibody, or fragment thereof, which recognizes a conformational epitope comprising amino acids 120-130 of α-Synuclein (α-Syn), and wherein affinity of the antibody for α-Syn fibrils is similar to that for α-Syn monomers. In some embodiments, the antibody binds to α-Syn monomers with an affinity equal to or tighter than about $10^{-9}$ M.

Provided is an isolated monoclonal antibody comprising a light chain variable region (VL) and a heavy chain variable region (VH), wherein the VL comprises a CDR1 region comprising the amino acid sequence of SEQ ID NOs: 1, 11 or 21; a CDR2 region comprising the amino acid sequence of SEQ ID NOs: 2, 12 or 22; and a CDR3 region comprising the amino acid sequence of SEQ ID NOs: 3, 13 or 23, and wherein the VH comprises a CDR1 region comprising the amino acid sequence of SEQ ID NOs: 6, 16 or 26; a CDR2 region comprising the amino acid sequence of SEQ ID NOs: 7, 17 or 27; and a CDR3 region comprising the amino acid sequence of SEQ ID NOs: 8, 18 or 28. In some embodiments, the VL comprises a CDR1 region comprising the amino acid sequence of SEQ ID NOs: 1 or 11; a CDR2 region comprising the amino acid sequence of SEQ ID NOs: 2 or 12; and a CDR3 region comprising the amino acid sequence of SEQ ID NOs: 3 or 13, and wherein the VH comprises a CDR1 region comprising the amino acid sequence of SEQ ID NOs: 6 or 16; a CDR2 region comprising the amino acid sequence of SEQ ID NOs: 7 or 17; and a CDR3 region comprising the amino acid sequence of SEQ ID NOs: 8 or 18. In some embodiments, the VL comprises a CDR1 region comprising the amino acid sequence of SEQ ID NO:1; a CDR2 region comprising the amino acid sequence of SEQ ID NO:2; and a CDR3 region comprising the amino acid sequence of SEQ ID NO: 3; and wherein the VH comprises a CDR1 region comprising the amino acid sequence of SEQ ID NO: 6; a CDR2 region comprising the amino acid sequence of SEQ ID NO: 7; and a CDR3 region comprising the amino acid sequence of SEQ ID NO:8. In some embodiments, the VL comprises a CDR1 region comprising the amino acid sequence of SEQ ID NO: 11; a CDR2 region comprising the amino acid sequence of SEQ ID NO: 12; and a CDR3 region comprising the amino acid sequence of SEQ ID NO: 13, and wherein the VH comprises a CDR1 region comprising the amino acid sequence of SEQ ID NO: 16; a CDR2 region comprising the amino acid sequence of SEQ ID NO: 17; and a CDR3 region comprising the amino acid sequence of SEQ ID NO: 18. In some embodiments, the VL comprises a CDR1 region comprising the amino acid sequence of SEQ ID NO:21; a CDR2 region comprising the amino acid sequence of SEQ ID NO: 22; and a CDR3 region comprising the amino acid sequence of SEQ ID NO: 23, and wherein the VH comprises a CDR1 region comprising the amino acid sequence of SEQ ID NO: 26; a CDR2 region comprising the amino acid sequence of SEQ ID NO: 27; and a CDR3 region comprising the amino acid sequence of SEQ ID NO: 28.

In some embodiments, the VL comprises the amino acid sequence of SEQ ID NOs: 4, 14 or 24, and wherein the VH comprises the amino acid sequence of SEQ ID NOs: 9, 19 or 29. In further embodiments, the VL comprises the amino acid sequence of SEQ ID NOs: 4 or 14, and wherein the VH comprises the amino acid sequence of SEQ ID NOs: 9 or 19.

In some embodiments:
(a) the VL comprises the amino acid sequence of SEQ ID NO: 4, and the VH comprises SEQ ID NO: 9;

(b) the VL comprises the amino acid sequence of SEQ ID NO: 14, and the VH comprises SEQ ID NO: 19; or
(c) the VL comprises the amino acid sequence of SEQ ID NO: 24, and the VH comprises SEQ ID NO: 29.

In some embodiments, the antibody is humanized. In further embodiments, the antibody is labeled.

Also provided is a pharmaceutical composition comprising the monoclonal antibody of any one of the preceding embodiments and at least one pharmaceutical excipient.

Also provided is an isolated polynucleotide comprising at least one of the nucleic acid sequences of SEQ ID NOs: 5, 10, 15, 20, 25 or 30. In some embodiments, the polynucleotide comprises:
(a) the nucleic acid sequences of SEQ ID NOs: 5 and 10;
(b) the nucleic acid sequences of SEQ ID NOs: 15 and 20; or
(c) the nucleic acid sequences of SEQ ID NOs: 25 and 30.

Provided is a method of treating a synucleopathic disease in a subject in need thereof, the method comprising administering to the subject a therapeutically effective amount of the isolated monoclonal antibody of any of the previous embodiments. In some embodiments, the synucleopathic disease is at least one from the group consisting of Parkinson's disease, Parkinson's disease with dementia, Dementia with Lewy bodies, Alzheimer's disease, Down's syndrome, multiple-system atrophy, prion diseases, and other α-Syn related neurodegenerative disorders. In further embodiments, the antibody is provided to the subject as a pharmaceutical composition. In yet further embodiments, the antibody is administered parenterally to the subject.

Provided is a method of detecting a synucleopathic disease in a subject, the method comprising administering to the subject a labeled isolated monoclonal antibody of any of the preceding embodiments, and detecting presence or absence of a complex of the labeled isolated monoclonal antibody with any α-Syn fibrils present in the subject, wherein, if the complex is detected, the subject has a synucleopathic disease.

Also provided is a method of detecting α-Syn fibrils in a sample, the method comprising contacting the sample with a labeled isolated monoclonal antibody of any of the preceding embodiments, and detecting presence or absence of a complex of the labeled isolated monoclonal antibody with any α-Syn fibrils present in the sample, wherein, if the complex is detected, α-Syn fibrils are present in the sample.

BRIEF DESCRIPTION OF THE DRAWINGS

The following detailed description of specific embodiments of the invention will be better understood when read in conjunction with the appended drawings. For the purpose of illustrating the invention, the drawings show specific embodiments. It should be understood, however, that the invention is not limited to the precise arrangements and instrumentalities of the embodiments shown in the drawings.

DETAILED DESCRIPTION OF THE INVENTION

Definitions

Figure 1A:
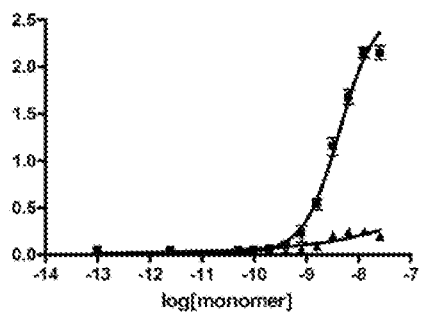
FIG. 1A is a pair of graphs depicting the affinity of mAb Syn9063.26.22 for human monomeric (top) and fibrillar (PFF) (bottom) α-Syn measured by sandwich ELISA. 384-well plates were coated with 0.3 µg of the indicated mAb. After blocking, these were incubated with various concentrations of α-Syn monomer or PFFs (expressed as monomer equivalent concentration) as indicated. MJF-R1 was used as a reporter antibody to determine affinity for each form of α-Syn.
Figure 1A:
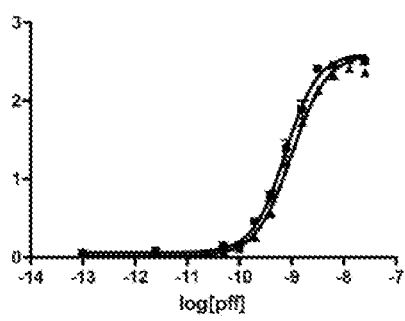

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, analytical chemistry, immunology, and nucleic acid chemistry and hybridization are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "α-Synuclein" or "α-Syn" or "α-syn" refers to a protein that is expressed mainly in brain tissues and is primarily located at the presynpatic terminal of neurons. In certain embodiments, the invention contemplates human α-Syn, which has the sequence SEQ ID NO: 31:

```
          10         20         30         40
    MDVFMKGLSK AKEGVVAAAE KTKQGVAEAA GKTKEGVLYV 50         60         70         80
    GSKTKEGVVH GVATVAEKTK EQVTNVGGAV VTGVTAVAQK 90        100        110        120
    TVEGAGSIAA ATGFVKKDQL GKNEEGAPQE GILEDMPVDP 130        140
    DNEAYEMPSE EGYQDYEPEA
```

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "affinity" for a molecule towards another refers to the degree (or tightness) of binding between the two molecules. A higher affinity means tighter binding between the two molecules. Affinity can be quantified in terms of dissociation constant (or $K_d$), where a $K_d$ value that is lower in magnitude (closer to zero) indicates a higher affinity.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

The term "antibody," as used herein, refers to an immunoglobulin molecule able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426). As used herein, a "neutralizing antibody" is an immunoglobulin molecule that binds to and blocks the biological activity of the antigen.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated or synthesized, or can be derived from a biological sample. Such a biological sample can include, but is not limited to a tissue sample, a tumor sample, a cell or a biological fluid.

A "coding region" of a gene consists of the nucleotide residues of the coding strand of the gene and the nucleotides of the non-coding strand of the gene that are homologous with or complementary to, respectively, the coding region of an mRNA molecule produced by transcription of the gene.

A "coding region" of an mRNA molecule also consists of the nucleotide residues of the mRNA molecule that are matched with an anti-codon region of a transfer RNA molecule during translation of the mRNA molecule or that encode a stop codon. The coding region may thus include nucleotide residues corresponding to amino acid residues not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "delivery vehicle" is used herein as a generic reference to any delivery vehicle capable of delivering a compound to a subject, including, but not limited to, dermal delivery vehicles and transdermal delivery vehicles.

The term "DNA" as used herein is defined as deoxyribonucleic acid.

"Effective amount" or "therapeutically effective amount" are used interchangeably herein, and refer to an amount of a compound, formulation, material, or composition, as described herein, effective to achieve a particular biological result. Such results may include, but are not limited to, treatment of a disease or condition as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between). As used herein, an antibody fragment refers to active fragments thereof, i.e., fragments having the same characteristics that are used for the definition of an antibody according to the invention, in certain embodiments high affinity for α-Syn fibrils (composed of misfolded α-Syn) and low or high binding affinity to α-Syn monomers. For convenience when the term antibody is used, fragments thereof exhibiting the same characteristic are also being considered.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

The term "recombinant DNA" as used herein is defined as DNA produced by joining pieces of DNA from different sources.

The term "recombinant polypeptide" as used herein is defined as a polypeptide produced by using recombinant DNA methods.

The term "RNA" as used herein is defined as ribonucleic acid.

The term "therapeutic" as used herein means a treatment and/or prophylaxis.

The term to "treat," as used herein, means reducing the frequency with which symptoms are experienced by a subject or administering an agent or compound to reduce the frequency and/or severity with which symptoms are experienced. As used herein, "alleviate" is used interchangeably with the term "treat."

As used herein, "treating a disease, disorder or condition" means reducing the frequency or severity with which a symptom of the disease, disorder or condition is experienced by a subject. Treating a disease, disorder or condition may or may not include complete eradication or elimination of the symptom.

The following abbreviations are used herein: CDR, complementary-determining region; DLB, dementia with Lewy bodies; MSA, multiple system atrophy; PD, Parkinson's disease; VH, heavy chain variable region; VL, light chain variable region.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This disclosure is generally directed to certain monoclonal (mouse) antibodies, or fragments thereof, that recognize α-Syn, a protein that is misfolded in Parkinson's disease and related neurodegenerative disorders known as synucleinopathies. Whereas the majority of antibodies against α-Syn have been generated using the soluble monomeric (i.e. native) form of the protein as an antigen, the present antibodies were raised against recombinant α-Syn that was misfolded into amyloid fibrils in vitro and resembles the pathological form found in human disease. It is demonstrated herein that the antibodies of the invention recognize α-Syn that accumulates in the brains of humans with Parkinson's disease. In certain embodiments, the antibodies of the invention recognize a conformational epitope comprising amino acids 110-120 of α-Syn. In other embodiments, the antibodies of the invention recognize a conformational epitope comprising amino acids 120-130 of α-Syn.

In certain embodiments, the antibodies of the invention show preferential binding towards the pathological form of α-Syn (i.e., fibrils) compared to the native (i.e., monomeric) form. In other embodiments, the antibodies of the invention reduce formation of pathological α-Syn inclusions/fibrils that normally form in cultured neurons that are exposed to recombinant α-Syn fibrils. In yet other embodiments, the antibodies of the invention detect pathological α-Syn fibrils. In yet other embodiments, the antibodies of the invention are used as therapeutics for decreasing the development/spread of pathological α-Syn fibrils in synucleinopathies. In yet other embodiments, the antibodies of the invention do not cross-react with Tau and/or beta-amyloid protein.

In certain embodiments, the antibodies of the invention bind to α-Syn fibrils with a dissociation constant $K_d$ equal to or less than about $10^{-6}$ M, about $10^{-7}$ M, about $10^{-8}$ M, about $10^{-9}$ M, about $10^{-10}$ M, or about $10^{-11}$ M. In other embodiments, the antibodies of the invention bind to α-Syn monomers with an affinity that at least about 10 times, 30 times, 100 times, 300 times, or 1000 times lower than the affinity of the antibodies for α-Syn fibrils. In yet other embodiments, the antibodies of the invention bind to α-Syn monomers with a dissociation constant $K_d$ equal to or higher than about $10^{-10}$ M, about $10^{-9}$ M, about $10^{-8}$ M, about $10^{-7}$ M, about $10^{-6}$ M, about $10^{-5}$ M, about $10^{-4}$ M, or about $10^{-3}$ M. In yet other embodiments, the antibodies of the invention bind with nearly equal affinity to α-Syn fibrils and monomers. In yet other embodiments, the antibodies of the invention bind with nearly equal affinity to α-Syn fibrils and monomers, with a dissociation constant $K_d$ equal to or less than about $10^{-7}$ M, about $10^{-8}$ M, about $10^{-9}$ M, about $10^{-10}$ M, or about $10^{-11}$ M. Binding affinities of the antibodies can be determined by using a variety of methods recognized in the art, including methods described elsewhere herein, such as but not limited to isothermal calorimetry, surface plasmon resonance, immunoassays such as ELISA or RIAs, and the like.

Compositions Comprising Antibodies

In one aspect, the invention comprises isolated monoclonal antibodies that selectively bind α-Syn in the fibrillar conformation, and/or bind both soluble and fibrillar α-Syn with high affinity. In certain embodiments, the antibody comprises a heavy chain. In other embodiments, the heavy chain comprises three complementary-determining regions (CDR), namely CDR1, CDR2 and CDR3. In yet other embodiments, the light chain comprises three complementary-determining region (CDR), namely CDR1, CDR2 and CDR3.

In certain embodiments, the monoclonal antibody is derived from hybridoma Syn9063.26.22 with light and heavy variable chains having the sequences shown below:

```
VL (Variable Light)
MHC978LC.2\;M13
CDR Analysis
SSVSY................_      DTS_              QQWRSYPPT
SEQ ID NO: 1                SEQ ID NO: 2      SEQ ID NO: 3

Amino Acid Sequence in FASTA format
>MHC978LC.2\;M13
QIVLTQSPAIMSASPGEKVTMTCSASSSVSYMYWYQQKPGSSPRLLIYDTSKLASGVP
VRFSGSGSGTSYSLTISRMEAEDAATYYCQQWRSYPPTFGAGTKLELK
SEQ ID NO: 4

Nucleotide Sequence in FASTA format
>MHC978LC.2\;M13
CAAATTGTTCTCACCCAGTCTCCAGCAATCATGTCTGCATCTCCAGGGGAGAAGG
TCACCATGACCTGCAGTGCCAGCTCAAGTGTAAGTTACATGTACTGGTACCAGCA
GAAGCCAGGATCCTCCCCCAGACTCCTGATTTATGACACATCCAAGCTGGCTTCT
GGCGTCCCTGTTCGCTTCAGTGGCAGTGGGTCTGGGACCTCTTACTCTCTCACAAT
CAGCCGAATGGAGGCTGAAGATGCTGCCACTTATTACTGCCAGCAGTGGAGAAG
TTACCCACCCACGTTCGGTGCTGGGACCAAGCTGGAGCTGAAA
SEQ ID NO: 5

VH (Variable Heavy)
MHC978HC.1\;M13
CDR Analysis
GFSLTSYG..._                IWSGGST..._       ARTFTTSTSAWFAY
SEQ ID NO: 6                SEQ ID NO: 7      SEQ ID NO: 8

Amino Acid Sequence in FASTA format
>MHC978HC.1\;M13
QVQLKQSGPGLVQPSQSQSLTCTVSGFSLTSYGVHWVRQPLGKGLEWLGVIWSGGS
TDYNAAFISRL SIRKDNSKSQVFFKMNSLQADDTAIYYCARTFTTSTSAWFAYWGQ
GTLVTVSA
SEQ ID NO: 9

Nucleotide Sequence in FASTA format
>MHC978HC.1\;M13
CAGGTGCAGCTGAAGCAGTCAGGACCTGGCCTAGTGCAGCCCTCACAGAGCCAG
TCCCTGACCTGCACAGTCTCTGGTTTCTCATTAACTAGTTATGGCGTACACTGGG
TTCGCCAGCCTCTAGGAAAGGGTCTGGAGTGGCTGGGAGTGATCTGGAGTGGTG
GAAGCACAGACTATAATGCTGCTTTCATATCCAGACTGAGCATCAGGAAGGACA
```

-continued

```
ACTCCAAGAGCCAAGTCTTCITTAAAATGAACAGTCTGCAAGCTGATGACACAG
CCATATACTACTGTGCCAGAACCTTTACTACGTCTACCTCGGCCTGGTTTGCTTA
CTGGGGCCAAGGGACTCTGGTCACTGTCTCTGCA
SEQ ID NO: 10
```

In certain embodiments, the monoclonal antibody is derived from hybridoma Syn9048.04.07 with the light and heavy variable chains having the sequences shown below:

```
VL (Variable Light)
MHC992LC.1\;M13
CDR Analysis
QSVLYSSNQKNY_         WAS_            HQYLSLFT
SEQ ID NO: 11         SEQ ID NO: 12   SEQ ID NO: 13

Amino Acid Sequence in FASTA format
>MHC992LC.1\;M13
NIMMTQSPS SLAVSAGEKVTMSCKSSQSVLYSSNQKNYLAWYQQKPGQSPKMLIYW
ASFRESGVPDRFTGSGSGTDFTLTISSVQAEDLAVYYCHQYLSLFTFGSGTKLEIK
SEQ ID NO: 14

Nucleotide Sequence in FASTA format
>MHC992LC.1\;M13
AACATTATGATGACACAGTCGCCATCATCTCTGGCTGTGTCTGCAGGAGAAAA
GGTCACTATGAGCTGTAAGTCCAGTCAAAGTGTTTTATACAGTTCAAATCAGAA
GAACTACTTGGCCTGGTACCAGCAGAAACCAGGGCAGTCTCCTAAAATGCTGA
TCTACTGGGCATCCTTTAGGGAATCTGGTGTCCCTGATCGCTTCACAGGCAGTG
GATCTGGGACAGATTTTACTCTTACCATCAGCAGTGTACAAGCTGAAGACCTGG
CAGTTTATTACTGTCATCAATACCTCTCCTTATTCACGTTCGGCTCGGGGACAA
AGTTGGAAATAAAA
SEQ ID NO: 15

VH (Variable Heavy)
MHC992HC.2\;M13
CDR Analysis
GYTFTTFY....         IYPVNVKI..      VRGGRGLDY
SEQ ID NO: 16        SEQ ID NO: 17   SEQ ID NO: 18

Amino Acid Sequence in FASTA format
>MHC992HC.2\;M13
QVQLQQSGPELVKPGASVRISCKASGYTFTTFYLHWVKQRPGQGLEWIGWIYPVNV
KIKYSERFKGKATLTADKSSSTAYMQLGSLTSEDSAVYFCVRGGRGLDYWGQGTTL
TVSS
SEQ ID NO: 19

Nucleotide Sequence in FASTA format
>MHC992HC.2\;M13
CAGGTCCAGCTGCAGCAGTCTGGACCTGAGCTGGTGAAGCCTGGGGCTTCAGTG
CGGATATCCTGCAAGGCTTCTGGCTACACCTTCACAACCTTCTATTTACACTGGG
TGAAGCAGAGGCCTGGACAGGGACTTGAGTGGATTGGATGGATTTATCCTGTAA
ATGTTAAAATTAAGTACAGTGAGAGGTTCAAGGGCAAGGCCACACTGACTGCAG
ACAAATCCTCCAGCACAGCCTACATGCAGCTCGGCAGCCTGACCTCTGAGGACT
CTGCGGTCTATTTCTGTGTAAGAGGGGGAGGGGACTTGACTACTGGGGCCAAG
GCACCACTCTCACAGTCTCCTCA
SEQ ID NO: 20
```

In certain embodiments, the monoclonal antibody is derived from hybridoma Syn9068.13.01 with the light and heavy variable chains having the sequences shown below:

```
VL (Variable Light)
MHC993LC.3\;M13
CDR Analysis
SSVTY...............  DTS             QQWSSNPPT
SEQ ID NO: 21          SEQ ID NO: 22   SEQ ID NO: 23

Amino Acid Sequence in FASTA format
>MHC993LC.3\;M13
QIVLTQSPAIMSASPGEKVTMTCSASSSVTYMHWYQQKSGTSPKRWIYDTSKLASGV
PARFSGSGSGTSYSLTISS
MEAEDAATYYCQQWSSNPPTFGGGTKLEIR
SEQ ID NO: 24
```

```
Nucleotide Sequence in FASTA format
>MHC993LC.3\;M13
CAAATTGTTCTCACCCAGTCTCCAGCAATCATGTCTGCATCTCCAGGGGAGAAGG
TCACCATGACCTGCAGTGCCAGCTCAAGTGTAACTTACATGCACTGGTACCAGC
AGAAGTCAGGCACCTCCCCCAAAAGATGGATTTATGACACATCCAAACTGGCTT
CTGGAGTCCCTGCTCGCTTCAGTGGCAGTGGGTCTGGGACCTCTTACTCTCTCAC
AATCAGCAGCATGGAGGCTGAAGATGCTGCCACTTATTACTGCCAGCAGTGGAG
TAGTAACCCACCCACGTTCGGAGGGGGGACCAAGCTGGAAATAAGA
SEQ ID NO: 25

VH (Variable Heavy)
MHC993HC.1\;M13
CDR Analysis
GFTFNTYA....          IRNKSNNYAT       VRGGLSPFDY
SEQ ID NO: 26         SEQ ID NO: 27    SEQ ID NO: 28

Amino Acid Sequence in FASTA format
>MHC993HC.1\;M13
EVHLVESGGGLVQPKGSLKLSCAASGFTFNTYAMHWVRQAPGKGLEWVARIRNK
SNNYATYYADSVKDRFTISRDD
SQSMLFLQMDNLKTEDTAIYYCVRGGLSPFDYWGQGTTLTVSS
SEQ ID NO: 29

Nucleotide Sequence in FASTA format
>MHC993HC.1\;M13
GAGGTACACCTTGTTGAGTCTGGTGGAGGATTGGTGCAGCCTAAAGGGTCATTG
AAACTCTCATGTGCAGCCTCTGGATTCACCTTCAATACCTACGCCATGCACTGG
GTCCGCCAGGCTCCAGGAAAGGGTTTGGAATGGGTTGCTCGCATAAGAAATAA
AAGTAATAATTATGCAACATATTATGCCGATTCAGTGAAAGACAGGTTCACCAT
CTCCAGAGATGATTCACAAAGCATGCTCTTTCTGCAAATGGACAACTTGAAAAC
TGAGGACACAGCCATATATTACTGTGTGAGAGGGGGGTTATCTCCCTTTGACTA
CTGGGGCCAAGGCACCACACTCACAGTCTCCTCA
SEQ ID NO: 30
```

In certain embodiments, the antibody comprises an immunoglobulin light chain variable region (VL) comprising the amino acid sequence of SEQ ID NOs: 4, 14 or 24. In other embodiments, the antibody comprises a VL comprising the amino acid sequence of SEQ ID NOs: 4 or 14.

In certain embodiments, the antibody comprises an immunoglobulin heavy chain variable region (VH) comprising the amino acid sequence of SEQ ID NOs: 9, 19 or 29. In other embodiments, the antibody comprises a VH comprising the amino acid sequence of SEQ ID NOs: 9 or 19.

In certain embodiments, the antibody comprises a VL comprising the amino acid sequence of SEQ ID NO:4, and a VH comprising SEQ ID NO: 9. In other embodiments, the antibody comprises a VL comprising the amino acid sequence of SEQ ID NO: 14, and a VH comprising SEQ ID NO: 19. In yet other embodiments, the antibody comprises a VL comprising the amino acid sequence of SEQ ID NO: 24, and a VH comprising SEQ ID NO: 29.

In certain embodiments, the antibody comprises a VL comprising: a CDR1 region comprising the amino acid sequence of SEQ ID NOs: 1, 11 or 21; a CDR2 region comprising the amino acid sequence of SEQ ID NOs: 2, 12 or 22; and a CDR3 region comprising the amino acid sequence of SEQ ID NOs: 3, 13 or 23. In other embodiments, the antibody comprises a VL comprising: a CDR1 region comprising the amino acid sequence of SEQ ID NOs: 1 or 11; a CDR2 region comprising the amino acid sequence of SEQ ID NOs: 2 or 12; and a CDR3 region comprising the amino acid sequence of SEQ ID NOs: 3 or 13.

In certain embodiments, the antibody comprises a VL comprising: a CDR1 region comprising the amino acid sequence of SEQ ID NO: 1; a CDR2 region comprising the amino acid sequence of SEQ ID NO: 2; and a CDR3 region comprising the amino acid sequence of SEQ ID NO: 3. In other embodiments, the antibody comprises a VL comprising: a CDR1 region comprising the amino acid sequence of SEQ ID NO: 11; a CDR2 region comprising the amino acid sequence of SEQ ID NO: 12; and a CDR3 region comprising the amino acid sequence of SEQ ID NO: 13. In yet other embodiments, the antibody comprises a VL comprising: a CDR1 region comprising the amino acid sequence of SEQ ID NO: 21; a CDR2 region comprising the amino acid sequence of SEQ ID NO: 22; and a CDR3 region comprising the amino acid sequence of SEQ ID NO: 23.

In certain embodiments, the antibody comprises a VH comprising: a CDR1 region comprising the amino acid sequence of SEQ ID NOs: 6, 16 or 26; a CDR2 region comprising the amino acid sequence of SEQ ID NOs: 7, 17 or 27; and a CDR3 region comprising the amino acid sequence of SEQ ID NOs: 8, 18 or 28. In other embodiments, the antibody comprises a VH comprising: a CDR1 region comprising the amino acid sequence of SEQ ID NOs: 6 or 16; a CDR2 region comprising the amino acid sequence of SEQ ID NOs: 7 or 17; and a CDR3 region comprising the amino acid sequence of SEQ ID NOs: 8 or 18.

In certain embodiments, the antibody comprises a VH comprising: a CDR1 region comprising the amino acid sequence of SEQ ID NO: 6; a CDR2 region comprising the amino acid sequence of SEQ ID NO: 7; and a CDR3 region comprising the amino acid sequence of SEQ ID NO: 8. In other embodiments, the antibody comprises a VH comprising: a CDR1 region comprising the amino acid sequence of SEQ ID NO: 16; a CDR2 region comprising the amino acid sequence of SEQ ID NO: 17; and a CDR3 region comprising the amino acid sequence of SEQ ID NO: 18. In yet other embodiments, the antibody comprises a VH comprising: a CDR1 region comprising the amino acid sequence of SEQ ID NO: 26; a CDR2 region comprising the amino acid sequence of SEQ ID NO: 27; and a CDR3 region comprising the amino acid sequence of SEQ ID NO: 28.

In certain embodiments, the antibody comprises a VL comprising: a CDR1 region comprising the amino acid sequence of SEQ ID NO: 1; a CDR2 region comprising the amino acid sequence of SEQ ID NO: 2; and a CDR3 region comprising the amino acid sequence of SEQ ID NO: 3; and a VH comprising: a CDR1 region comprising the amino acid sequence of SEQ ID NO: 6; a CDR2 region comprising the amino acid sequence of SEQ ID NO: 7; and a CDR3 region comprising the amino acid sequence of SEQ ID NO: 8. In other embodiments, the antibody comprises a VL comprising: a CDR1 region comprising the amino acid sequence of SEQ ID NO: 11; a CDR2 region comprising the amino acid sequence of SEQ ID NO: 12; and a CDR3 region comprising the amino acid sequence of SEQ ID NO: 13; a VH comprising: a CDR1 region comprising the amino acid sequence of SEQ ID NO: 16; a CDR2 region comprising the amino acid sequence of SEQ ID NO: 17; and a CDR3 region comprising the amino acid sequence of SEQ ID NO: 18. In yet other embodiments, the antibody comprises a VL comprising: a CDR1 region comprising the amino acid sequence of SEQ ID NO: 21; a CDR2 region comprising the amino acid sequence of SEQ ID NO: 22; and a CDR3 region comprising the amino acid sequence of SEQ ID NO: 23; and a VH comprising: a CDR1 region comprising the amino acid sequence of SEQ ID NO: 26; a CDR2 region comprising the amino acid sequence of SEQ ID NO: 27; and a CDR3 region comprising the amino acid sequence of SEQ ID NO: 28.

The invention further provides isolated polynucleotides (including RNA and/or DNA) encoding the antibodies or antigen binding fragments thereof, for example a nucleic acid encoding for one or more CDRs, or a variable heavy chain or variable light chain region of the α-Syn antibodies of the invention. Nucleic acid includes DNA and RNA.

In certain embodiments, the antibody has a VL encoded by the nucleic acid sequence of SEQ ID NOs: 5, 15 or 25. In other embodiments, the antibody has a VL encoded by the nucleic acid sequence of SEQ ID NOs: 5 or 15. In yet other embodiments, the antibody has a VH encoded by the nucleic acid sequence of SEQ ID NOs: 10, 20 or 30. In yet other embodiments, the antibody has a VH encoded by the nucleic acid sequence of SEQ ID NOs: 10 or 20.

In certain embodiments, the invention provides an isolated polynucleotide comprising the nucleic acid sequence of SEQ ID NOs: 5, 15 or 25. In other embodiments, the invention provides an isolated polynucleotide comprising the nucleic acid sequence of SEQ ID NOs: 5 or 15. In yet other embodiments, the invention provides an isolated polynucleotide comprising the nucleic acid sequence of SEQ ID NOs: 10, 20 or 30. In yet other embodiments, the invention provides an isolated polynucleotide comprising the nucleic acid sequence of SEQ ID NOs: 10 or 20.

In certain embodiments, the invention provides an isolated polynucleotide comprising a nucleic acid encoding the amino acid sequence of SEQ ID NOs: 4, 14 or 24. In other embodiments, the invention provides an isolated polynucleotide comprising a nucleic acid encoding the amino acid sequence of SEQ ID NOs: 4 or 14. In yet other embodiments, the invention provides an isolated polynucleotide comprising a nucleic acid encoding the amino acid sequence of SEQ ID NOs: 9, 19 or 29. In yet other embodiments, the invention provides an isolated polynucleotide comprising a nucleic acid encoding the amino acid sequence of SEQ ID NOs: 9 or 19.

The invention further provides a host cell comprising the expression vector. In certain embodiments, the host cell is isolated. In other embodiments, the host cell is a non-human cell. The expression vector can comprise nucleic acid sequences that direct and/or control expression of the inserted polynucleotide. Such nucleic acid sequences can include regulatory sequence, including promoter sequences, terminator sequences, polyadenylation sequences, and enhancer sequences. Systems for cloning and expression of a polypeptide in a variety of cells are well known in the art.

The antibody of the invention can be a mammalian antibody, such as primate, human, rodent, rabbit, ovine, porcine or equine antibody. The antibody can be any class or isotype antibody, for example IgM or IgG. In certain embodiments, the antibody is IgG.

The invention further provides a kit comprising an antibody of the invention. The antibody may be an intact immunoglobulin molecule or fragment thereof such as Fab, F(ab)2 or Fv fragment. The antibody can be labelled as described elsewhere herein. The kit can be for use in a method of determining whether a subject has a neurodegenerative disease, and/or for treating a subject afflicted or thought to be afflicted with a neurodegenerative disease. The kit can further any other reagent or instrument that is required to implement a method of the invention, such as a buffer, an applicator, and the like.

Figure 1B:
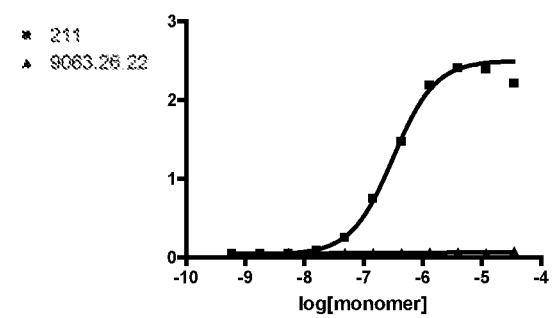
FIG. 1B is a pair of graphs depicting the affinity of mAb Syn9048.04.07 for human monomeric (top) and fibrillar (PFF) (bottom) α-Syn measured by sandwich ELISA. 384-well plates were coated with 0.3 µg of the indicated mAb. After blocking, these were incubated with various concentrations of α-Syn monomer or PFFs (expressed as monomer equivalent concentration) as indicated. MJF-R1 was used as a reporter antibody to determine affinity for each form of α-Syn.
Figure 1B:
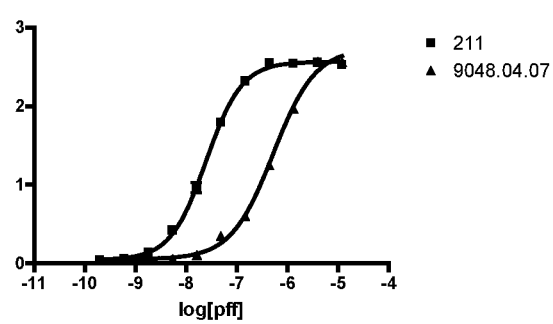
Figure 1C:
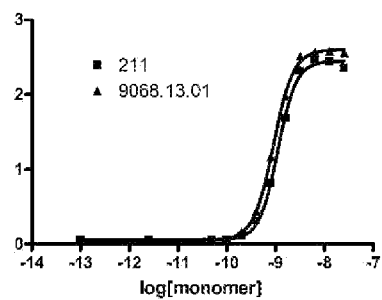
FIG. 1C is a pair of graphs depicting the affinity of mAb Syn9068.13.01 for human monomeric (top) and fibrillar (PFF) (bottom) α-Syn measured by sandwich ELISA. 384-well plates were coated with 0.3 µg of the indicated mAb. After blocking, these were incubated with various concentrations of α-Syn monomer or PFFs (expressed as monomer equivalent concentration) as indicated. MJF-R1 was used as a reporter antibody to determine affinity for each form of α-Syn. Performance of three subclones show greater binding to human PFFs over monomer for 9063.26.22 and 9048.04.07. For each of FIGS. 1A-1C, curve fitting was done using the software package GraphPad. All experiments were performed in triplicate and the numbers reported are the average ELISA values from those experiments.
Figure 1C:
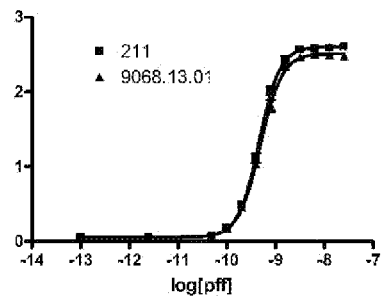

The non-limiting generation of these antibodies is illustrated in Example 1. Data showing preferential binding of α-Syn fibrils over monomer is presented in FIGS. 1A-1B, high affinity binding to both α-Syn fibrils and monomer in FIG. 1C, and these properties are further described in FIGS. 2-4. In certain embodiments, the invention comprises pharmaceutical compositions comprising each of these antibodies in combination with one or more pharmaceutically acceptable excipients. In some embodiments the pharmaceutical composition is formulated for parenteral delivery. In other embodiments, the antibodies are humanized.

Method of Treating a Synucleopathic Disease

In another aspect, the invention provides a method of treating a synucleopathic disease comprising administering a therapeutically effective amount of an isolated monoclonal antibody of the invention to a patient. In certain embodiments, the antibody is humanized. In other embodiments, the antibody is administered as a pharmaceutical composition.

Figure 3:
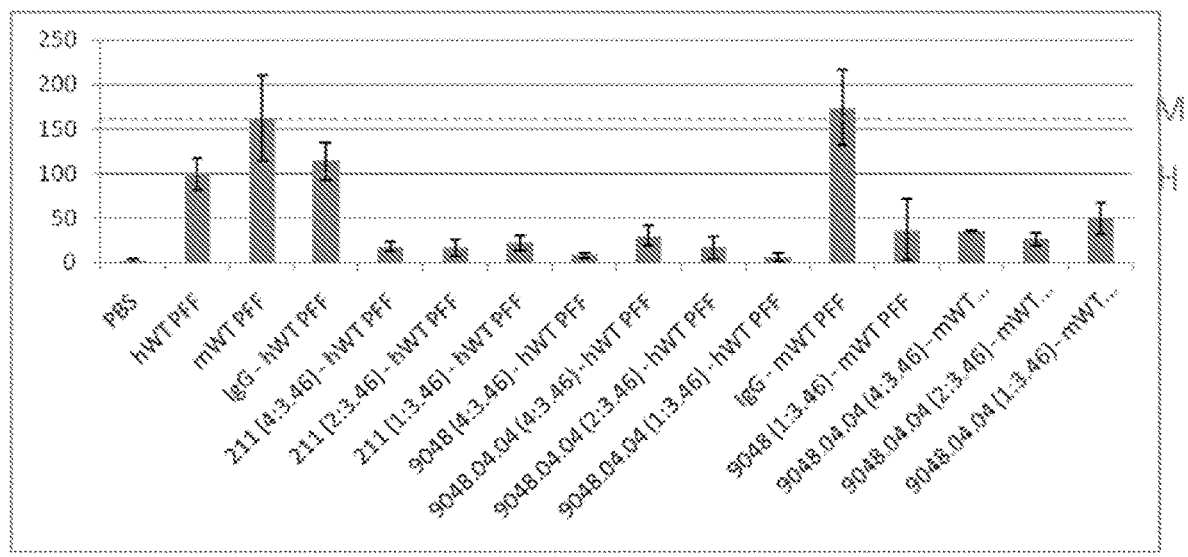
FIG. 3 is a graph depicting data from an experiment in which primary hippocampal neurons from embryonic CD1 mice were plated in 96-well plates (17,500 cells per well). After 7 days in vitro (DIV), cells were pre-treated for 30 mins with either nonspecifc mouse IgG (IgG), Syn211, or Syn9048.04.07 at the indicated mAb:PFF ratios. Cells were then treated with PBS, hWT α-Syn pffs or mWT α-Syn pffs (0.125 µg/well each) and fixed 7 days later in 4% PFA. Neurons were immunostained with mAb 81A to detect p-α-Syn positive pathology. The graph shows mean levels of p-α-Syn pathology after different mAb treatments. Horizontal lines represent the extent of p-α-Syn positive pathology in neurons treated only with mWT α-Syn PFFs (M) or hWT α-Syn PFFs (H).
Figure 4A:
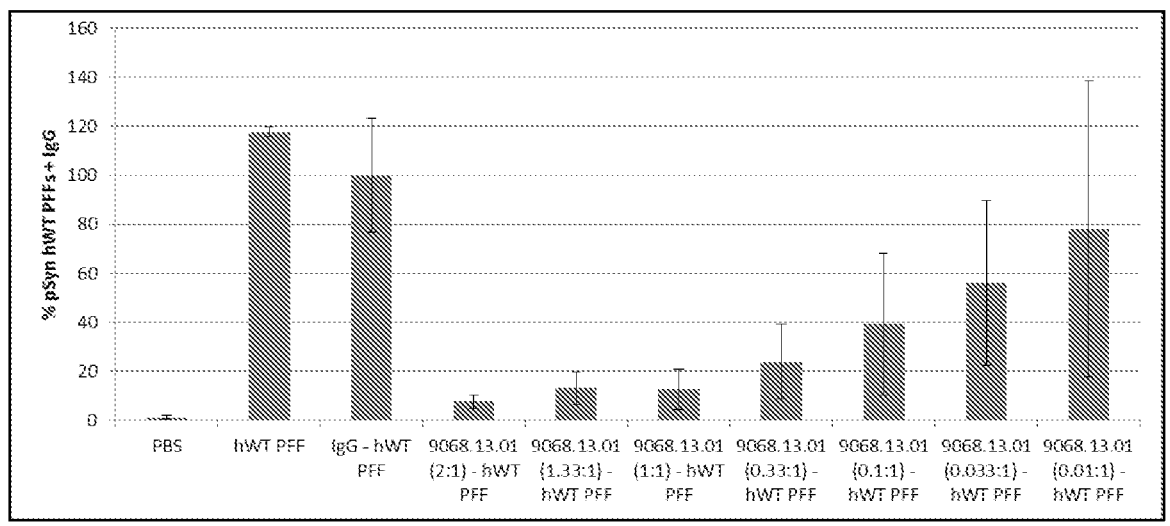
FIGS. 4A and 4B are a pair of graphs depicting data from an experiment in which primary hippocampal neurons from embryonic CD1 mice were plated in 96-well plates (17,500 cells per well). After 7 days in vitro (DIV), cells were pre-treated for 30 mins with either nonspecifc mouse IgG (IgG) or Syn9068.13.01 at the indicated mAb:PFF ratios. Cells were then treated with PBS, hWT α-Syn PFFs (FIG. 4A), or mWT, or hWT α-Syn PFFs (FIG. 4B; 0.125 µg/well each) and fixed 7 days later in 4% PFA. Neurons were immunostained with mAb 81A to detect p-α-Syn positive pathology. The graphs show mean levels of p-α-Syn pathology after different mAb treatments.
Figure 4B:
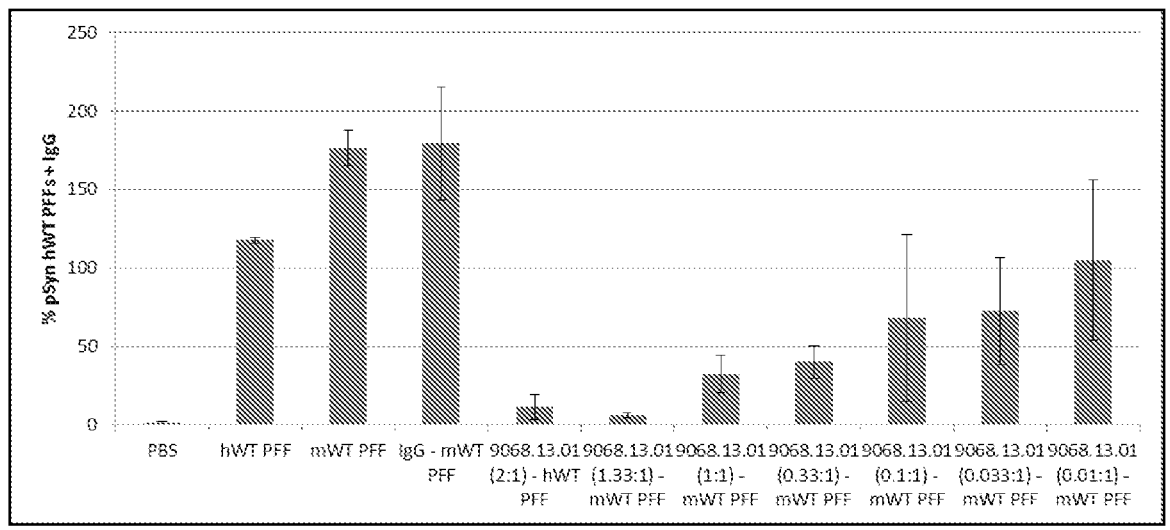

The monoclonal antibodies described above may be used to treat synucleopathic disease by reducing α-Syn pathology in neurons induced by α-Syn fibrils, as shown in FIGS. 3 and 4 and further described in Example 3. In certain embodiments, the neurodegenerative disorders associated with α-Syn include but are not limited to Parkinson's disease, dementia (such as Parkinson's disease with dementia and/or dementia with Lewy bodies), Alzheimer's disease, Down's syndrome, multiple-system atrophy, prion diseases, and other α-Syn related neurodegenerative disorders. The antibody can be administered systemically or directly to the site where α-Syn fibrils, e.g. a Lewy body, are observed or thought to be present. In a non-limiting example, the antibody can be administered by injection into a blood vessel supplying the brain or into the brain itself. The subject can be a mammal, such as a human or a non-human mammal.

In some embodiments, administration of the antibody may result in a preservation in dopamine production in the brain. In some embodiments, the preservation in dopamine production is an increase in striatal dopamine production.

Methods of Detecting a Synucleopathic Disease

In yet another aspect, the invention provides methods of detecting synucleopathic disease in a patient. In other embodiments, the antibodies of the invention can be used as diagnostic tools for neurodegenerative disorders associated with α-Syn, including but not limited to Parkinson's disease, dementia (such as Parkinson's disease with dementia and/or dementia with Lewy bodies), Alzheimer's disease, Down's syndrome, multiple-system atrophy, prion diseases, and other α-Syn related neurodegenerative disorders.

In certain embodiments, the method of detecting synucleopathic disease in a subject comprises the steps of administering a labeled, isolated monoclonal antibody of the invention to the subject, and detecting the presence of absence of a complex between any α-Syn fibrils in the subject and the antibody. If the complex is present, that indicates that α-Syn fibrils exist in the subject. In certain embodiments, if α-Syn fibrils are present in the subject, the subject has a neurodegenerative disease. In other embodiments, if α-Syn fibrils are not present in the subject, the subject does not have a neurodegenerative disease. In yet other embodiments, if the subject has a neurodegenerative disease, the individual is counseled to undergo therapy and/or pharmacological treatment for the neurodegenerative disease. In yet other embodiments, if the subject has a neurodegenerative disease, the individual is provided therapy and/or pharmacological treatment for the neurodegenerative disease.

In certain embodiments, the method further comprises comparing the level of antibody/α-Syn fibrils complex formed in the subject with the level of antibody/α-Syn fibrils complex formed in a reference subject. The reference subject can be a subject known not to have α-Syn fibrils, a subject known to have detectable α-Syn fibrils, and/or a subject known to have a certain level of α-Syn fibrils. The reference subject can further be the same subject being treated or evaluated, but corresponding to an earlier α-Syn fibrils detection experiment, as a way to evaluate disease progression and/or treatment efficacy in the subject.

In yet another aspect, the invention provides methods of detecting α-Syn fibrils in a sample. In certain embodiments, the antibodies of the invention can be used as diagnostic tools for detecting the presence of α-Syn fibrils in a sample.

In certain embodiments, the method of detecting α-Syn fibrils in a sample (for example, from a subject) comprises the steps of contacting the sample with a labeled, isolated monoclonal antibody of the invention, and detecting the presence or absence of a complex between any α-Syn fibrils in the sample and the antibody. If the complex is detected, that indicates the presence of α-Syn fibrils in the sample. The sample can be, in non-limiting examples, cerebrospinal fluid (CSF), blood, urine, saliva, or tissues from brain, gut, colon, skin, or salivary gland. In certain embodiments, the sample is a CSF sample and/or a brain tissue sample. In other embodiments, the sample is used as is after being removed from the subject. In other embodiments, the sample is pre-treated being used within the present methods.

In certain embodiments, the method further comprises comparing the level of antibody-α-Syn fibrils complex formed in the sample with the level of antibody-α-Syn fibrils complex formed in a reference sample. The reference sample can be from a subject known not to have α-Syn fibrils, a subject known to have detectable α-Syn fibrils, and/or a subject known to have a certain level of α-Syn fibrils. The reference sample can further be from the same subject being treated or evaluated, but corresponding to an earlier α-Syn fibrils detection, as a way to evaluate disease progression and/or treatment efficacy in the subject. In certain embodiments, the level of α-Syn fibrils detected in a subject or in a sample from a subject correlates with severity or progression of a neurodegenerative disease in the subject. In other embodiments, the methods of the invention can be used to monitor severity or progression of a neurodegenerative disease in the subject. In yet other embodiments, the methods of the invention can be used to monitor effectiveness of a therapy and/or pharmacological intervention in a subject afflicted or believed to be afflicted with a neurodegenerative disease.

Methods for detecting formation of a complex between the antibody and α-Syn fibrils comprise, but are not limited to, radioimmunoassay, enzyme-linked immunosorbant assay (ELISA), sandwich immunoassay, fluorescent immunoassay, precipitation reaction, gel immunodiffusion assay, agglutination assay, protein A immunoassay, immunoelectrophoresis assay, electrophoresis, western blotting, or any other technique known in the art.

The antibodies of the invention can be combined with a label and used to detect α-Syn fibrils in a patient or in a sample. Methods of labeling antibodies are known in the art and a variety of approaches may be employed. In certain embodiments the label is a radiolabel, such as but not limited to $F^{18}$, $I^{123}$, $In^{111}$, $I^{131}$, $C^{14}$, $H^3$, $Tc^{99m}$, $P^{32}$, $I^{125}$, $Ga^{68}$ and the like. In other embodiments, the label is a fluorescent label, such as but not limited to fluorescein, rhodamine and the like. In yet other embodiments, the label is a contrast agent, such as but not limited to gadolinium (Gd), dysprosium and iron, magnetic agents, and the like. Other labels include nuclear magnetic resonance active labels, positron emitting isotopes detectable by a PET scanner, chemiluminescent and enzymatic markers. Non-limiting imaging techniques include electron microscopy, confocal microscopy, light microscopy, positron emission tomography (PET), gamma-scintigraphy, magnetic resonance imaging (MRI), functional magnetic resonance imaging (FMRI), magnetoencephalography (MEG), and single photon emission computerized tomography (SPECT). In yet other embodiments, the label is on a secondary antibody that binds a primary antibody comprising the above described sequences.

Administration/Dosage/Formulations

Administration of the compounds and/or compositions of the present invention to a patient, preferably a mammal, more preferably a human, may be carried out using known procedures, at dosages and for periods of time effective to perform an imaging method contemplated in the invention. An effective amount of the therapeutic compound necessary for adequate signal for imaging may vary according to factors such as the state of a disease or disorder in the patient; the age, sex, and weight of the patient; and the equipment used to detect the compound of the invention. One of ordinary skill in the art would be able to study the relevant factors and make the determination regarding the effective amount of the therapeutic and/or imaging compound without undue experimentation.

Actual dosage levels of the active ingredients in the pharmaceutical compositions of this invention may be varied so as to obtain an amount of the active ingredient that is effective to achieve successful imaging for a particular patient, composition, and mode of administration, without being toxic to the patient.

In certain embodiments, the compositions of the invention are formulated using one or more pharmaceutically acceptable excipients or carriers. In certain embodiments, the pharmaceutical compositions of the invention comprise an effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the preferred embodiments of the present invention, and are not to be construed as limiting in any way the remainder of the disclosure.

Example 1: Generation of Monoclonal Antibodies Against Aggregated α-Syn

Syn9063.26.22, Syn9048.04.07 and Syn9068.13.01 are mouse monoclonal antibodies (mAbs) generated from mice immunized with aggregated recombinant WT human α-Syn bearing strain-B conformation. Preparation of this antigen is described in Guo et al., 2013, Cell. 2013 154(1):103-17. Hybridomas were generated, and subcloned twice by single cell dilution. Clonality was confirmed by sequencing. RNA was extracted from subclones and amplified using RACE/PCR. Variable regions (H+L) were sequenced using VBASE2 to assign complementarity determining regions (CDRs).

The properties of 9000 series mAbs are presented below in Table 1:

TABLE 1

Figure 2:
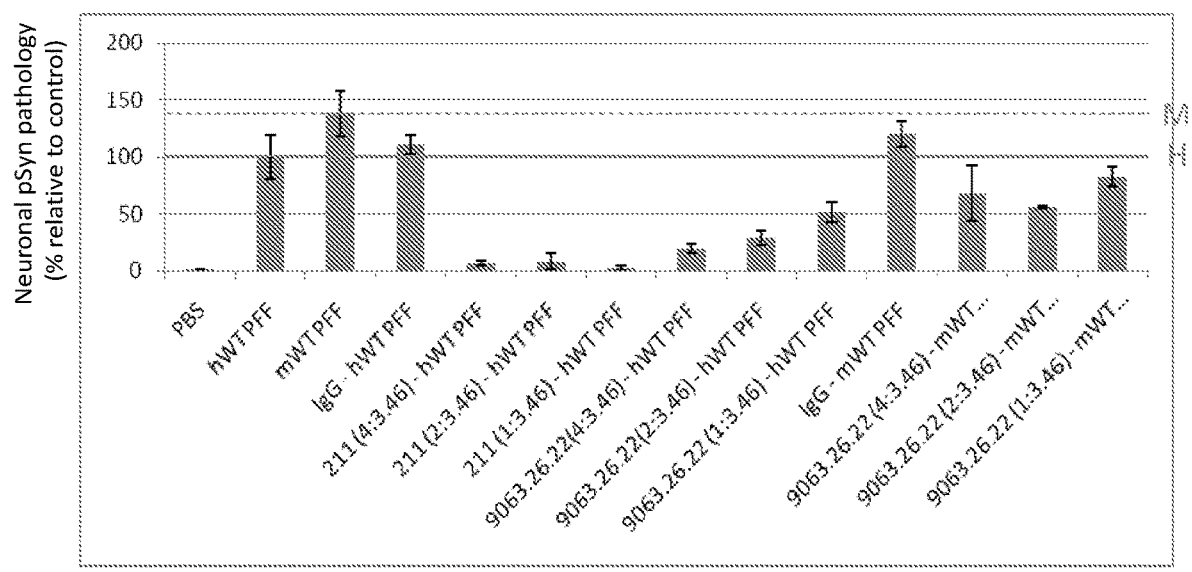
FIG. 2 is a graph depicting data from an experiment in which primary WT hippocampal neurons from embryonic CD1 mice were plated in 96-well plates (17,500 cells per well). After 7 days in vitro (DIV), cells were pre-treated for 30 mins with either nonspecifc mouse IgG (IgG), Syn211, or Syn9063.26.22 at the indicated mAb:PFF ratios. Cells were then treated with PBS, human wild-type hWT α-Syn PFFs, or mouse wild-type (mWT) α-Syn PFFs (0.125 µg/well) and fixed 7 days later in 4% PFA. Neurons were immunostained with mAb 81A to detect p-α-Syn positive pathology. The graph shows mean levels of p-α-Syn pathology from triplicate samples from 2 independent experiments. Horizontal lines represent the extent of p-α-Syn positive pathology in neurons treated only with mWT α-Syn PFFs (M) or hWT α-Syn PFFs (H).

| Property/criteria | Syn9063.26.22 | Syn9048.04.07 | Syn9068.13.01 |
| --- | --- | --- | --- |
| Epitope | 110-120 | 110-120 | 120-130 |
| Isotype | IgG2b | IgG1 | IgG1 |
| Recognition of Hu vs. Ms αSyn (direct ELISA) | 1.1-fold | 1.4-fold | 1.0-fold |
| Selective binding to PFFs (sandwich ELISA) | 100-fold | 30-fold | none |
| Inhibition in neuron assay (Hu PFFs); see FIGS. 2-4 | ↓80% | ↓>95% | ↓85% |
| Inhibition in neuron assay (Ms PFFs); see FIGS. 2-4 | ↓50% | ↓>95% | ~90% |
| IHC on human tissue | Strong | Strong | Strong |
| IHC on mouse tissue | Strong | Strong | Strong |

Hu PFFs, recombinant human preformed αSyn fibrils; Ms PFF, recombinant mouse preformed αSyn fibrils; IHC, immunohistochemistry Example 2: Affinity of Syn9063.26.22, Syn9048.04.07, 9068.13.01 for α-Syn Monomer Vs. Fibrils The affinity of three mAbs from the 9000 series for human monomeric and fibrillar (PFF) α-Syn was measured by sandwich ELISA. 384-well plates were coated with 0.3 ug of the indicated mAb. After blocking, these were incubated with various concentrations of α-Syn monomer or PFFs as indicated. MJR-R1 was used as a reporter antibody to determine affinity for each form of α-Syn. Subclones 9063.26.22 and 9048.04.07 show greater binding to human PFFs than monomer. Curve fitting was done using the software package GraphPad. All experiments were performed in triplicate and the numbers reported are the average ELISA values from those experiments. The data are presented in FIGS. 1A-1C.

Example 3: Syn9063.26.22, Syn9048.04.07 and Syn 9068.13.01 Reduce α-Syn Pathology in Neurons Induced by α-Syn Fibrils Primary WT hippocampal neurons from CD1 mice were plated in 96-well plates (17,500 cells per well). After 7 days in vitro (DIV), cells were pre-treated for 30 mins with either nonspecifc mouse IgG (IgG), Syn211, Syn9063.26.22, Syn9048.04.07 at the indicated mAb:α-Syn PFF ratios. Cells were then treated with PBS, hWT α-Syn PFFs, or mWT α-Syn PFFs (0.125 μg/well) and fixed 7 days later in 4% PFA. Neurons were immunostained with mAb 81A to detect p-α-Syn positive pathology. Graph shows mean levels of p-α-Syn pathology from triplicate samples from 2 independent experiments. The data are presented in FIG. 2 (Syn9063.26.22) or FIG. 3 (Syn9048.04.07).

Primary WT neurons from CD1 mice were plated in 96-well plates (17,500 cells per well). After 7 days in vitro (DIV), cells were pre-treated for 30 mins with either non-specifc mouse IgG (IgG) or Syn9068.13.01 at the indicated mAb:α-Syn PFF ratios. Cells were then treated with PBS, hWT α-Syn PFFs (upper panel), or mWT α-Syn PFFs (lower panel; 0.125 μg/well each) and fixed 7 days later in 4% PFA. Neurons were immunostained with mAb 81A to detect p-α-Syn positive pathology. Graph shows mean levels of p-α-Syn pathology after different mAb treatments. The data are presented in FIGS. 4A-4B.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated monoclonal antibody comprising a light chain variable region (VL) and a heavy chain variable region (VH),
   wherein the VL comprises
      a CDR1 region comprising the amino acid sequence of SEQ ID NO: 1;
      a CDR2 region comprising the amino acid sequence of SEQ ID NO: 2; and
      a CDR3 region comprising the amino acid sequence of SEQ ID NO: 3; and
   wherein the VH comprises
      a CDR1 region comprising the amino acid sequence of SEQ ID NO: 6;
      a CDR2 region comprising the amino acid sequence of SEQ ID NO: 7; and
      a CDR3 region comprising the amino acid sequence of SEQ ID NO: 8.

2. The monoclonal antibody of claim 1, wherein the VL comprises the amino acid sequence of SEQ ID NO: 4, and wherein the VH comprises the amino acid sequence of SEQ ID NO: 9.

3. The monoclonal antibody of claim 1, which is humanized.

4. The monoclonal antibody of claim 1, which is labeled.

5. A pharmaceutical composition comprising the monoclonal antibody of claim 1 and at least one pharmaceutical excipient.

6. An isolated monoclonal antibody comprising a light chain variable region (VL) and a heavy chain variable region (VH),
   wherein the VL comprises
      a CDR1 region comprising the amino acid sequence of SEQ ID NO: 11;
      a CDR2 region comprising the amino acid sequence of SEQ ID NO: 12; and
      a CDR3 region comprising the amino acid sequence of SEQ ID NO: 13,
   and
   wherein the VH comprises
      a CDR1 region comprising the amino acid sequence of SEQ ID NO: 16;
      a CDR2 region comprising the amino acid sequence of SEQ ID NO: 17; and
      a CDR3 region comprising the amino acid sequence of SEQ ID NO: 18.

7. The monoclonal antibody of claim 6, wherein the VL comprises the amino acid sequence of SEQ ID NOs: 14, and wherein the VH comprises the amino acid sequence of SEQ ID NOs: 19.

8. The monoclonal antibody of claim 6, which is humanized.

9. The monoclonal antibody of claim 6, which is labeled.

10. A pharmaceutical composition comprising the monoclonal antibody of claim 6 and at least one pharmaceutical excipient.

11. A method of treating a synucleopathic disease in a subject in need thereof, the method comprising administering to the subject a therapeutically effective amount of the isolated monoclonal antibody of claim 6.

12. The method of claim 11, wherein the synucleopathic disease is at least one from the group consisting of Parkinson's disease, Parkinson's disease with dementia, Dementia with Lewy bodies, Alzheimer's disease, Down's syndrome, multiple-system atrophy, prion diseases, and other α-Syn related neurodegenerative disorders.

13. The method of claim 11, wherein the antibody is provided to the subject as a pharmaceutical composition.

14. The method of claim 13, wherein the antibody is administered parenterally to the subject.

15. A method of detecting a synucleopathic disease in a subject, the method comprising administering to the subject a labeled isolated monoclonal antibody of claim 6, and detecting presence or absence of a complex of the labeled isolated monoclonal antibody with any α-Syn fibrils present in the subject,
   wherein, if the complex is detected, the subject has a synucleopathic disease.

16. A method of detecting α-Syn fibrils in a sample, the method comprising contacting the sample with a labeled isolated monoclonal antibody of claim 6, and detecting presence or absence of a complex of the labeled isolated monoclonal antibody with any α-Syn fibrils present in the sample,
   wherein, if the complex is detected, α-Syn fibrils are present in the sample.

17. An isolated monoclonal antibody comprising a light chain variable region (VL) and a heavy chain variable region (VH),
   wherein the VL comprises
      a CDR1 region comprising the amino acid sequence of SEQ ID NO: 21;
      a CDR2 region comprising the amino acid sequence of SEQ ID NO: 22; and
      a CDR3 region comprising the amino acid sequence of SEQ ID NO: 23, and
   wherein the VH comprises
      a CDR1 region comprising the amino acid sequence of SEQ ID NO: 26;
      a CDR2 region comprising the amino acid sequence of SEQ ID NO: 27; and
      a CDR3 region comprising the amino acid sequence of SEQ ID NO: 28.

18. The monoclonal antibody of claim 17, wherein
   the VL comprises the amino acid sequence of SEQ ID NO: 24, and the VH comprises SEQ ID NO: 29.

19. The monoclonal antibody of claim 17, which is humanized.

20. The monoclonal antibody of claim 17, which is labeled.

21. A pharmaceutical composition comprising the monoclonal antibody of claim 17 and at least one pharmaceutical excipient.

22. An isolated polynucleotide comprising at least one of the nucleic acid sequences of SEQ ID NOs: 5, 10, 15, 20, 25 or 30.

23. The polynucleotide of claim 22, comprising
   (a) the nucleic acid sequences of SEQ ID NOs: 5 and 10;
   (b) the nucleic acid sequences of SEQ ID NOs: 15 and 20; or
   (c) the nucleic acid sequences of SEQ ID NOs: 25 and 30.

* * * * *